(12) United States Patent
McKay

(10) Patent No.: US 8,926,710 B2
(45) Date of Patent: Jan. 6, 2015

(54) OSTEOINDUCTIVE BONE GRAFT INJECTABLE CEMENT

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 391 days.

(21) Appl. No.: 12/911,351

(22) Filed: Oct. 25, 2010

(65) Prior Publication Data

US 2012/0100225 A1    Apr. 26, 2012

(51) Int. Cl.
| | |
|---|---|
| A61F 2/28 | (2006.01) |
| A61L 27/54 | (2006.01) |
| A61K 38/18 | (2006.01) |
| A61L 27/12 | (2006.01) |
| A61L 27/36 | (2006.01) |
| A61L 27/58 | (2006.01) |
| A61L 24/00 | (2006.01) |
| A61L 24/02 | (2006.01) |

(52) U.S. Cl.
CPC ............. *A61K 38/1875* (2013.01); *A61L 27/12* (2013.01); *A61L 27/3608* (2013.01); *A61L 27/365* (2013.01); *A61L 27/54* (2013.01); *A61L 27/58* (2013.01); *A61L 24/0015* (2013.01); *A61L 24/0042* (2013.01); *A61L 24/02* (2013.01); *A61L 2300/406* (2013.01); *A61L 2300/414* (2013.01); *A61L 2430/02* (2013.01)
USPC ...................... 623/23.63; 623/23.58; 424/549; 424/683

(58) Field of Classification Search
None
See application file for complete search history.

(56) References Cited

U.S. PATENT DOCUMENTS

| | | | |
|---|---|---|---|
| 6,458,375 B1 * | 10/2002 | Gertzman et al. ............ 424/423 |
| 6,764,517 B2 | 7/2004 | Yamamoto et al. |
| 6,863,694 B1 | 3/2005 | Boyce et al. |
| 7,291,345 B2 | 11/2007 | Winterbottom et al. |
| 7,494,950 B2 | 2/2009 | Armitage et al. |
| 7,582,309 B2 | 9/2009 | Rosenberg et al. |
| 7,621,963 B2 | 11/2009 | Simon et al. |
| 7,658,940 B2 | 2/2010 | Constantz |
| 7,754,246 B2 | 7/2010 | Moseley et al. |
| 2002/0018796 A1 | 2/2002 | Wironen |
| 2002/0098222 A1 | 7/2002 | Wironen et al. |
| 2002/0193883 A1 | 12/2002 | Wironen |
| 2004/0002558 A1 | 1/2004 | McKay |
| 2006/0233849 A1 * | 10/2006 | Simon et al. ................... 424/422 |
| 2007/0098756 A1 | 5/2007 | Behnam |
| 2007/0178130 A1 | 8/2007 | McKay et al. |
| 2007/0218144 A1 | 9/2007 | Lally |
| 2008/0033572 A1 | 2/2008 | D'Antonio et al. |
| 2008/0069852 A1 * | 3/2008 | Shimp et al. ................... 424/423 |
| 2008/0119859 A1 * | 5/2008 | Lally ............................... 606/76 |
| 2008/0188946 A1 | 8/2008 | Rosenberg et al. |
| 2009/0074871 A1 | 3/2009 | Sunwoo et al. |
| 2009/0130173 A1 | 5/2009 | Behnam et al. |
| 2009/0226523 A1 | 9/2009 | Behnam et al. |
| 2009/0257914 A1 | 10/2009 | Christopher et al. |
| 2009/0318982 A1 | 12/2009 | Genin et al. |

FOREIGN PATENT DOCUMENTS

| | | |
|---|---|---|
| WO | 2004045372 A2 | 6/2004 |
| WO | 2008117043 A2 | 10/2008 |

OTHER PUBLICATIONS

Dinopoulous et al, "Safety and efficacy of use of dimineralised bone matrix in orthopaedic and trauma surgery" Expert Opinion, 2006, vol. 5, No. 6, pp. 847-866.*
International Search Report and Written Opinion for PCT/US2011/054795 mailed on May 4, 2012, the counterpart application.
International Search Report and Written Opinion for PCT/US2011/056210, the counterpart application, mailed on May 23, 2012.

* cited by examiner

*Primary Examiner* — Allison Fox
(74) *Attorney, Agent, or Firm* — Sorell Lenna & Schmidt LLP

(57) ABSTRACT

Osteoconductive bone graft materials are provided. These compositions contain injectable cements and demineralized bone matrix fibers. The combination of these materials enables the filling of a bone void while balancing strength and resorption.

20 Claims, No Drawings

OSTEOINDUCTIVE BONE GRAFT INJECTABLE CEMENT

BACKGROUND

An aging population carries with it an increased risk for injuries and deterioration of tissue and bone. Similarly, the more physically active a population is, the more its members put themselves at risk for these types of harm to their bodies.

Some of these injuries will result in the deterioration, chipping, displacement or otherwise removing of pieces of bone. When bone is removed, a bone void is left in its place, which can result in both pain an structural weakness.

Both medical practitioners and patients would prefer to have the bone voids filled. However, when selecting materials to fill these voids one must be mindful of at least three things. First, one would prefer to use a material that can be sufficiently load-bearing. Second, one would prefer to use a material that can be manipulated into a desired size and shape. Third, one would prefer to use a material that facilitates natural bone growth and/or grafting.

Injectable cements are known products for filling bone voids with which medical practitioners that are skilled in this art are familiar. Because of their formulations, they can be manipulated and formulated to provide desirable load-bearing in voids in which they are inserted. Unfortunately, known technologies do not sufficiently optimize natural bone growth, while bearing the desired loads.

Accordingly, there is a need for novel and non-obvious injectable settable cements that provide an acceptable level of structural support while permitting bone regrowth.

SUMMARY

Compositions and methods for injecting bone graft materials into bone defects or bone grafting sites are provided. Through use of various embodiments of the present invention one may fill bone voids while both achieving sufficient load bearing and inducing bone formation.

In one embodiment, the present invention provides a bone graft material comprising demineralized bone matrix fibers and an injectable settable cement, wherein the demineralized bone matrix fibers comprise between about 20% and about 60% by volume of the bone graft material.

In some embodiments, the present invention provides materials and methods that result in a superior composition can provide initial fracture stability and bone grafting efficacy due to the presence of highly osteoinductive demineralized bone matrix fibers. While providing stability, the composition can foster de novo bone growth by the host organism.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Any numerical value inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

The headings below are not meant to limit the disclosure in any way. Embodiments under any one heading may be used in conjunction with embodiments under any other heading.

DEFINITIONS

It is noted that, as used in this specification and the appended claims, the singular forms "a," "an," and "the," include plural referents unless expressly and unequivocally limited to one referent.

The phase "demineralized bone matrix" refers to an acid extraction of bone, resulting in loss of most, if not all, of the mineralized component but retention of collagen and noncollagenous proteins, including growth factors. This type of bone can be used to make the graft material. Demineralized bone, in some embodiments, includes bone that has been partially, fully, segmentally or superficially (surface) demineralized. The efficacy of a demineralized bone matrix (DBM) as a bone-graft substitute or extender may be related to the total amount of bone morphogenetic protein (BMP) present, and the ratios of the different BMPs present. BMPs belong to the transforming growth factor (TGF) superfamily of proteins.

The term "autograft" as utilized herein refers to tissue intended for implantation that is extracted from the intended recipient of the implant.

The term "allograft" as utilized herein refers to tissue intended for implantation that is taken from a different member of the same species as the intended recipient.

The term "xenogenic" as utilized herein refers to material intended for implantation obtained from a donor source of a different species than the intended recipient. For example, when the implant is intended for use in an animal such as a horse (equine), xenogenic tissue of, e.g., bovine, porcine, caprine, etc., origin may be suitable.

The term "transgenic" as utilized herein refers to tissue intended for implantation that is obtained from an organism that has been genetically modified to contain within its genome certain genetic sequences obtained from the genome of a different species. The different species is usually the same species as the intended implant recipient but such limitation is merely included by way of example and is not intended to limit the disclosure here in anyway whatsoever.

The expressions "whole bone" and "substantially fully mineralized bone" refer to bone containing its full or substantially full, original mineral content that can be used.

The expression "substantially fully demineralized bone" as utilized herein refers to bone containing less than about 8% of its original mineral context. This type of bone can be used to make the graft material.

The term "mammal" refers to organisms from the taxonomy class "mammalian," including but not limited to humans, other primates such as chimpanzees, apes, orangutans and monkeys, rats, mice, cats, dogs, cows, horses, etc. In various embodiments, the mammal is a human patient.

The term "practitioner" or "user" means a person who is using the compositions, methods and/or devices of the current disclosure on a patient. These terms include, without limitation, doctors (e.g., surgeons, interventional specialists, and physicians), nurses, nurse practitioners, other medical personnel, clinicians, veterinarians, or scientists.

The term "syringe" refers to a device that has a needle, a barrel and plunger. Material may be placed in the barrel through the needle by drawing back upon the plunger, which is in the barrel. The negative pressure in the barrel draws the material through a hollow needle and up into the barrel. Alternatively, material may be placed into the barrel through a different opening that preferably is subsequently closed prior to dispensing the material for the syringe. Material can be dispensed by pushing down upon the plunger.

In some embodiments, the graft material can be malleble, cohesive, followable and/or can be shaped into any shape before it hardens. The term "malleable" includes that the graft material is capable of being permanently converted from a first shape to a second shape by the application of pressure.

The term "cohesive" as used herein means that the graft material tends to remain a singular, connected mass upon movement, including the exhibition of the ability to elongate substantially without breaking upon stretching.

The term "flowable" refers to a characteristic of a graft material whereby it can be passed through a conduit, such as a cannula or needle, by exerting a hydraulic pressure in the conduit.

The term "injectable" includes that the material can be placed at the target tissue site by extrusion of such material from the end of a cannula, needle, tube, orifice, or the like.

The graft material may be osteogenic. The term "osteogenic" as used herein includes the ability of the graft material to enhance or accelerate the growth of new bone tissue by one or more mechanisms such as osteogenesis, osteoconduction and/or osteoinduction.

The graft material may be osteoinductive. The term "osteoinductive" as used herein includes the ability of a substance to recruit cells from the host that have the potential for forming new bone and repairing bone tissue. Most osteoinductive materials can stimulate the formation of ectopic bone in soft tissue.

The graft material may be osteoconductive. The term "osteoconductive" as utilized herein includes the ability of a non-osteoinductive substance to serve as a suitable template or substrate along which bone may grow.

The term "treating" and the phrases "treatment of a disease" and "treatment of a condition" refer to executing a protocol that may include the use of the compositions, devices and methods herein and/or administering one or more bone materials to a patient (human, normal or otherwise, or other mammal), in an effort to alleviate signs or symptoms of the disease or condition. Alleviation can occur prior to signs or symptoms of the disease or condition appearing, as well as after their appearance. Thus, "treating" or "treatment" includes "preventing" or "prevention" of disease or undesirable condition. In addition, "treating" or "treatment" does not require complete alleviation of signs or symptoms, does not require a cure, and specifically includes protocols that have only a marginal effect on the patient.

DBM Fibers

Demineralized bone matrix (DBM) is well known for being highly osteoinductive. Thus, it induces the formation of bone tissue. In some embodiments, the DBM contains fibers of demineralized bone and one or more growth factors.

The DBM fibers may be present with cancellous bone chips. In some embodiments, the bone chips have a size of from about 1 mm to about 10 mm in diameter across their largest dimension or from about 2 mm to about 4 mm or from about 4 mm to about 6 mm or from about 6 mm to about 8 mm or from about 8 mm to about 10 mm across the largest dimension. A combined product of DBM fibers and cancellous bone chips is available as Grafton DBM®.

In some embodiments, the DBM fibers have an average length in the range of from about 250 micrometers to about 2 millimeters or from about 250 micrometers to about 750 micrometers or from about 750 micrometers to about 1.25 millimeters or from about 1.25 millimeters to about 2 millimeters.

As persons of ordinary skill in the art are aware, fibers have an aspect ratio, which is the average length to average thickness. In some embodiments, the aspect ratio is from about 4 to about 100 or from about 4 to about 25 or from about 25 to about 50 or from about 50 to about 75 or from about 75 to about 100.

In some embodiments, the average thickness of the fibers is from about 50 micrometers to about 250 micrometers or from about 50 micrometers to about 100 micrometers or from about 100 micrometers to about 150 micrometers or from about 150 micrometers to about 200 micrometers or from about 200 micrometers to about 250 micrometers.

Methods for preparing DBM fibers are known to persons of ordinary skill in the art and include but are not limited to shaving cortical bone (either defatted or undefatted) into thin shavings or plates, e.g., less than 250 micrometers. During shaving, the natural bone lamellae or osteons should be aligned within the plane of the shavings or plates. After shaving, the resulting shavings are subjected to demineralization so as to reduce their inorganic content to low levels. If not already defatted, the bone fragments may be defatted at this time. During the demineralization process, the material may be subjected to agitation in order to cause delamination of the bone fibers. This results in fine rope-like DBM fibers.

The fibers may be rinsed with water and/or a buffer in order to remove the solubalized mineral and excess acid. In some embodiments, this process is continued until the fibers have less than 5%, less than 4%, less than 3%, less than 2%, less than 1% or less than 0.5% residual calcium. Subsequently, they may be dried by, for example, oven drying or lyophilization.

In some embodiments, the DBM fibers can be obtained from sources, such as for example, preformed fiber sheets, matrices, or workable putties under the trade names Grafton® DBM Putty, Grafton® DBM Flex, and Grafton® DBM Matrix from Osteotech Corporation (Shrewsbury, N.J.).

In some embodiments, the DBM fibers have an average width to average thickness ratio of less than about 5. In some embodiments, the graft material may optionally contain DBM particles having an aspect ratio of less than about 3.

In some embodiments, the graft material may optionally contain an additive that modifies the composition's handling characteristics; however, such an additive is not required to maintain a minimal acceptable level of cohesiveness. In some embodiments, this additive at least partially coats the DBM fibers. The additive may be a biocompatible polymer, such as a water-soluble cellulosic (e.g. carboxymethyl cellulose), or a natural polymer, such as gelatin. The additive may be added to either the dry DBM component or the liquid component. The additive may be used to at least partially coat the DBM fibers prior to combining them with the liquid carrier. Non-limiting examples of additives suitable for use in the DBM composition include gelatin, carboxymethyl cellulose, hydroxypropyl methylcellulose, methylcellulose, hydroxyethyl cellulose, other cellulose derivatives, alginate, hyaluronic acid, collagen, sodium salts, polyvinyl pyrrolidones, polyvinyl alcohol, arabic gum, guar gum, xantham gum, chitosans, poloxamers or a combination thereof.

In some embodiments, the graft material can comprise DBM fibers and a biocompatible liquid in the range from 1:10 to 10:1, or 1:4 or 4:1, or about 1:1. The liquid may be any biocompatible liquid, including water, saline solution, buffered solutions, serum, bone marrow aspirant, blood, platelet-rich plasma or the like or mixtures thereof.

In some embodiments, the DBM fibers for the graft material are obtained from cortical autogenic, cortical allogenic, cortical xenogeneic, cancellous autogenic, cancellous allogenic, cancellous xenogeneic, corticocancellous autogenic, corticocancellous allogenic, or corticocancellous xenogeneic bone.

In some embodiments, the graft material includes a dry component, comprising DBM fibers having an average fiber length in the range from about 250 micrometers to about 2 mm and an average aspect ratio of greater than about 4, and a biocompatible fluid in an amount to provide a coherent formable mass. The DBM fibers are present in an amount greater than 40 wt % of said dry component.

In some embodiments, a collection of DBM fibers is provided, of which at least about 25 wt % have an average fiber length in the range from about 250 micrometers to about 2 mm and an aspect ratio of greater than about 4.

In some embodiments, a DBM implant is provided having a predetermined shape, wherein the DBM implant comprises DBM fibers having an average fiber length in the range from about 250 micrometers to about 2 mm and an aspect ratio of greater than about 4 and a biocompatible liquid in an amount to produce a coherent, and malleable mass. In some embodiments, the DBM implant has a density in the range of about 0.3 g/cc to about 0.7 g/cc. In some embodiments, the DBM implant has a compression strength greater than about 10 MPa. In some embodiments, the graft material comprising the DBM fibers is injectable through an 18-gauge needle.

Injectable Settable Cements

Injectable settable bone cements are compositions that are in a form that permits a practitioner to inject the cement through, e.g., a syringe. After being injected, the cement can set i.e., harden where it is deposited or be manipulated into a desired shape and then deposited prior to hardening. A non-limiting example of an injectable settable cement is Bone Solutions OsteoCrete™ Mg.

In some embodiments, the cement is designed to provide initial fracture stability, and to have relatively good cohesiveness prior to setting. The cement may also have a desirable resorption rate.

In some embodiments, the cement comprises a flow additive. Examples of flow additives include but are not limited to, hyaluronic acid, a hyaluronic salt, a sodium phosphate salt or a combination thereof.

In some embodiments, the cement comprises one or more, if not all, of $KH_2PO_4$, a metal oxide (e.g., MgO), a calcium containing compound (e.g., tricalcium phosphate), a sugar or sugar derivative and water. For example it may contain 35-65% $KH_2PO_4$, 25-45% of metal oxide, 3-12% $Ca_{10}(PO_4)_6(OH)_2$ and 0.5-8% sugar. The percentages of each of these components are weight based and are recited relative to the total amount of those components. The aforementioned components may be combined with water such that the aforementioned components combine to form 55-85% or 65-75% of the resulting product and water is the remaining 15-45% or 25-35%.

The metal oxide may be subjected to a calcination process. Calcination durations and temperatures are determined empirically, depending on the final characteristics and setting times desired. Generally, however, calcination temperatures of up to 1300° C. for up to several hours are typical.

After calcination, the oxide powder is mixed with MKP, a calcium containing compound and sugar. One method for sizing and homogenizing the various powders is via vibratory milling. Another homogenization method utilizes a ribbon mixer wherein the particles are ground to a fine size. However, aqueous versions (or other forms i.e., gels etc.) of some of the components can also be utilized. Additionally, generally pharmaceutical grade compounds are utilized. Sterilization of the various components may be required using sterilization techniques known in the art. Upon homogenization wherein all of the constituents are contained in a dry homogeneous mixture, water (or other aqueous solution) may be added up to about 45% of the weight of the resulting slurry although the amount of water can be adjusted to form a material of varying viscosity. The slurry may, for example, be mixed for between 1-10 minutes. Mixing can be achieved by a variety of techniques used in the art including by hand and electric mixing.

The cement can be created in injectable, paste, putty and other forms. The form may be dependent on the consistency of the material, which as noted above can be manipulated by varying the amount of water added to the dry mixture. Increasing the water content generally increases the flowability, while decreasing the water content tends to thicken the slurry.

Bone Graft Materials

The compositions of the present invention comprise the injectable settable cement, the DBM fibers and optionally the bone particles described above. These compositions may be used as bone graft materials. The compositions may also comprise one or more of the following substances, binders, fillers, meshes, substances providing radiopacity, plasticizers, biostatic/biocidal agents, surface active agents and combinations thereof.

The injectable cement may be combined with the DBM fibers to form a composition that has a more rapid resorption rate than the cement alone. In some embodiments, the resorption rate is increased by 5% to 40% or 5% to 15% or 15% to 25% or 25% to 40%. In some embodiments, resorption of the composition that contains both the cement and DBM fibers is within eight months, within seven months, within six months or within five months. In some embodiments, resorption is within four to seven months, or four to six months. Resorption may be completed between 85% or 99% within the aforementioned time periods.

The cement's inherent resorption rate exposes the DBM fibers and thus induces de novo bone formation and subsequent union of fractured bones or filling of bone defects. The addition of the DBM fibers may also increase the rate of cement resorption, which is desirable when using an osteoinductive bone grafting material.

In some embodiments, the composition of the present invention comprises about 20% to about 60% by volume of DBM fibers (or combination of DBM fibers and bone chips) or about 20% to about 50% by volume of DBM fibers (or combination of DBM fibers and bone chips) or about 20% to about 40% DBM fibers (or combination of DBM fibers and bone chips) or about 30% to about 60% DBM fibers (or combination of DBM fibers and bone chips) or about 30% to about 50% DBM fibers (or combination of DBM fibers and bone chips) or about 30% to about 40% DBM fibers (or combination of DBM fibers and bone chips) or about 40% to about 50% DBM fibers (or combination of DBM fibers and bone chips).

By way of non limiting examples, suitable binders that may be present include but are not limited to biological adhesives such as fibrin glue, fibrinogen, thrombin, mussel adhesive protein, silk, elastin, collagen, casein, gelatin, albumin, keratin, chitin or chitosan; cyanoacrylates; epoxy-based compounds; dental resin sealants; bioactive glass ceramics (such as apatite-wollastonite); dental resin cements; glass ionomer cements; nonbioabsorbable polymer such as polyacrylate, polymethyl methacrylate, polytetrafluoroethylene, polyurethane, polyamide; gelatin-resorcinol-formaldehyde glues; collagen-based glues; acrylic resins; bioabsorbable polymers such as starches, polyglycolide, polylactide, glycolide-lactide copolymers, polycaprolactone, polycarboxylic acids and their copolymers, polycarbonates, polyorthoesters, polyamino acids, polycyanoacrylates, polyhydroxybutyrate, polyhydroxyvalyrate, polyphosphazenes, polyvinylpyrrolidone, poly-propylene fumarate, poly-propylene fumarate-diacrylate, poly(propylene glycol-co-fumaric acid), tyrosine-based polycarbonates, pharmaceutical tablet binders (such as Eudragit® binders available from Hulls America, Inc.), polyvinylpyrrolidone, cellulose, ethyl cellulose, microcrystalline cellulose and blends thereof; nonbioabsorbable polymers such as polyacrylate, polymethylmethacrylate, polytetrafluroethylene, polyurethane and polyamide; etc., derivatives and blends of the foregoing are also suitable. When employed, the binder will typically represent from about 0.1 to about 5 weight percent of the composition. In some embodiments, the preferred binder is glycolide-lactide copolymer.

Suitable fillers that may be present include but are not limited to graphite or pyrolytic carbon; bioceramics; bioglass or other bioceramic or natural or synthetic polymers, e.g., bioabsorbable polymers such as polyglycolide, polylactide, glycolidelactide copolymer, and the like; nonbioabsorbable materials such as starches, polymethyl methacrylate, polytetrafluoroethylene, polyurethane, polyethylene and nylon; anorganic bone (i.e., bone mineral only, with the organic constituents removed), dentin tooth enamel, aragonite, calcite, nacre, amorphous calcium phosphate, hydroxyapatite, tricalcium phosphate and other calcium phosphate materials; calcium salts; etc. and mixtures of any of the foregoing. When employed, a filler will typically represent from about 0.1 to about 5 weight percent of the composition. In some embodiments, the preferred fillers are ceramics, particularly hydroxyapatite and mineralized cortical bone powder.

In some embodiments, the bone graft material includes magnesium. In some embodiments, the bone graft material comprises from about 1% to about 50% magnesium by weight based on the total weight of the bone graft material. In some embodiments, the bone graft material comprises about 54 wt % monopotassium phosphate, magnesium oxide 33 wt %, tricalcium phosphate 9 wt %, and dextrose 4 wt % as described in AJVR, Vol. 70, No. 8, (August 2009) and Am J Vet Res. 2007 April; 68 (4):370-8. The entire disclosures are herein incorporated by reference into the present disclosure. Magnesium in the composition enhances bone stability and healing.

Suitable fibers include but are not limited to carbon fibers (graphite or diamond); collagen fibers; tendon or ligament derived fibers; keratin; catgut; silk; cellulose; chitosan; suture materials, e.g., PLA/PGA and other copolymers; polyethylene; Teflon®; polyurethanes; Bioglass®; hydroxyapatite and other calcium phosphate materials in whisker or fiber shape; Aluminum oxide; etc. When employed, fibers will typically represent from about 0.1 to about 5 weight percent of the composition. In some embodiments, the preferred fiber is a collagen fiber.

Examples of meshes that may be used include, but are not limited to fabric or mesh structures containing the above identified fibers; metallic meshes, e.g., titanium and alloys, tantalum, stainless steels, cobalt chrome alloys, gold, silver, platinum; etc. When employed, mesh will typically represent from about 0.1 to about 5 weight percent of composition, calculated prior to forming the shaped material. In some embodiments, the preferred mesh is titanium mesh.

Examples of substances imparting radiopacity that may be used include but are not limited to barium and iodine containing compounds or compositions, e.g., barium sulfate and barium sulfate for suspension, Iopanoic acid, or the like. When employed, substances imparting radiopacity will typically represent from about 0.1 to about 5 weight percent of the composition. In some embodiments, the preferred substance imparting radioapacity is barium sulfate.

Suitable plasticizers that may be used include but are not limited to liquid polyhydroxy compounds such as glycerol, monoacetin, diacetin, pluronics, polyoxymers, block copolymers, oils, gels of colloidal clays, aqueous gels of organic polymers such as gelatin, pectin, methyl cellulose and high-molecular-weight polyethylene glycol; thixotropic agents such as aluminum hydroxide gel and aluminum phosphate gel, solution of polyvinyl alcohol, polyvinylpyrrolidone, cellulosic ester such as hydroxypropyl methylcellulose, carboxyl methylcellulose, pectin, foodgrade texturizing agent, gelatin, dextran, collagen, starch, hydrolyzed polyacrylonitrile, hydrolyzed polyacrylamide, polyelectrolyte such as polyacrylic acid salt, hydrogels, gels of colloidal clays, aqueous gels of organic polymers, such as gelatin agar, pectin methylcellulose, and high-molecular weight polyethylene glycol, chitosan, other materials that can suspend particles. When employed, the plasticizer will typically represent from about 0.1 to about 5 weight percent of the composition. In some embodiments, the preferred plasticizer is glycerol.

Suitable biostatic/biocidal agents that may be used include but are not limited to antibiotics, povidone, sugars, mucopolysaccharides, chlorobutanol, quarternary ammonium compounds such as benzalkonium chloride, organic mercurials, parahydroxy benzoates, aromatic alcohols, halogenated phenols, sorbic acid, benzoic acid, dioxin, EDTA, BHT, BHA, TBHQ, gallate esters, NDGA, tocopherols, gum guaiac, lecithin, boric acid, citric acid, p-Hydroxy benzoic acid esters, propionates, sulfur dioxide and sulfites, nitrates and nitrites of potassium and sodium, diethyl pyrocarbonate, sodium diacetate, diphenyl, hexamethylene tetramine o-phenyl phenol, and sodium o-phenylphenoxide, etc. When employed, biostatic/biocidal agents will typically represent from about 0.1 to about 5 weight percent of the composition. In some embodiments, the preferred biostatic/biocidal agent is antibiotic drugs.

Suitable surface active agents that may be used agents include but are not limited to the biocompatible nonionic, cationic, anionic and amphoteric surfactants and mixtures thereof. When employed, surface active agent will typically represent from about 0.1 to about 5 weight percent of the composition.

Additionally, the DBM fibers and/or the bone chips when present may be combined with any of a variety of medically and/or surgically useful substances that can be incorporated in, or associated with, the materials before, during, or after combination with the cement. Thus, e.g., one or more of such substances can be introduced into the bone-derived elements (i.e., the DBM or bone chips), e.g., by soaking or immersing the bone-derived elements in a solution or dispersion of the desired substance(s), or by adding the substance(s) directly to the osteogenic bone graft material. Medically/surgically useful substances include physiologically or pharmacologically active substances that act locally or systemically in the host.

The medically/surgically useful substances include but are not limited to bioactive substances that can be readily combined with the bone-derived element such as collagen, insoluble collagen derivatives, etc., and soluble solids and/or liquids dissolved therein; antiviricides, particularly those effective against HIV and hepatitis; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc.; biocidal/biostatic sugars such as dextran, glucose, etc.; amino acids; peptides; vitamins; inorganic elements; co-factors for protein synthesis; hormones; endocrine tissue or tissue fragments; synthesizers; enzymes such as alkaline phosphatase, collagenase, peptidases, oxidases, etc.; polymer cell scaffolds with parenchymal cells; angiogenic agents and polymeric carriers containing such agents; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors or other means; tissue transplants; demineralized bone powder; autogenous tissues such as blood, serum, soft tissue, bone marrow, etc.; bioadhesives; bone morphogenic proteins (BMPs); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, e.g., interleukin-1 (IL-1), interleukin-2 (IL-2); human alpha thrombin; transforming growth factor (TGFbeta); insulin-like growth factors (IGF-1, IGF-2); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immuno-suppressants; permeation enhancers, e.g., fatty acid esters such as laureate, myristate and stearate monoesters of polyethylene glycol, enamine derivatives, alpha-keto aldehydes, etc.; and nucleic acids. The amounts of such optionally added substances can vary widely with optimum levels being readily determined in a specific case by routine experimentation. In some embodiments, these substances will be present in a range of about 1 to about 10 percent or about 1 to about 5 percent or about 2 to about 4 percent, based on the total weight of the composition prior to implantation. The preferred medically/surgically useful substance is bone morphogenic proteins.

In exemplary embodiments, the graft material may comprise at least one growth factor. These growth factors include osteoinductive agents (e.g., agents that cause new bone growth in an area where there was none) and/or osteoconductive agents (e.g., agents that cause ingrowth of cells into and/or through the graft material). Osteoinductive agents can be polypeptides or polynucleotides compositions. Polynucleotide compositions of the osteoinductive agents include, but are not limited to, isolated Bone Morphogenic Protein (BMP), Vascular Endothelial Growth Factor (VEGF), Connective Tissue Growth Factor (CTGF), Osteoprotegerin, Growth Differentiation Factors (GDFs), Cartilage Derived Morphogenic Proteins (CDMPs), Lim Mineralization Proteins (LMPs), Platelet derived growth factor, (PDGF or rhPDGF), Insulin-like growth factor (IGF) or Transforming Growth Factor beta (TGF-beta) polynucleotides. Polynucleotide compositions of the osteoinductive agents include, but are not limited to, gene therapy vectors harboring polynucleotides encoding the osteoinductive polypeptide of interest. Gene therapy methods often utilize a polynucleotide, which codes for the osteoinductive polypeptide operatively linked or associated to a promoter or any other genetic elements necessary for the expression of the osteoinductive polypeptide by the target tissue. Such gene therapy and delivery techniques are known in the art (see, for example, International Publication No. WO90/11092, the disclosure of which is herein incorporated by reference in its entirety). Suitable gene therapy vectors include, but are not limited to, gene therapy vectors that do not integrate into the host genome. Alternatively, suitable gene therapy vectors include, but are not limited to, gene therapy vectors that integrate into the host genome.

In some embodiments, the polynucleotide is delivered in plasmid formulations. Plasmid DNA or RNA formulations refer to polynucleotide sequences encoding osteoinductive polypeptides that are free from any delivery vehicle that acts to assist, promote or facilitate entry into the cell, including viral sequences, viral particles, liposome formulations, lipofectin, precipitating agents or the like. Optionally, gene therapy compositions can be delivered in liposome formulations and lipofectin formulations, which can be prepared by methods well known to those skilled in the art. General methods are described, for example, in U.S. Pat. Nos. 5,593,972, 5,589,466, and 5,580,859, the disclosures of which are herein incorporated by reference in their entireties.

Gene therapy vectors further comprise suitable adenoviral vectors including, but not limited to for example, those described in U.S. Pat. No. 5,652,224, which is herein incorporated by reference.

Polypeptide compositions of the isolated osteoinductive agents include, but are not limited to, isolated Bone Morphogenic Protein (BMP), Vascular Endothelial Growth Factor (VEGF), Connective Tissue Growth Factor (CTGF), Osteoprotegerin, Growth Differentiation Factors (GDFs), Cartilage Derived Morphogenic Proteins (CDMPs), Lim Mineralization Proteins (LMPs), Platelet derived growth factor, (PDGF or rhPDGF), Insulin-like growth factor (IGF) or Transforming Growth Factor beta (TGF-beta707) polypeptides. Polypeptide compositions of the osteoinductive agents include, but are not limited to, full length proteins, fragments or variants thereof.

Variants of the isolated osteoinductive agents include, but are not limited to, polypeptide variants that are designed to increase the duration of activity of the osteoinductive agent in vivo. Typically, variant osteoinductive agents include, but are not limited to, full length proteins or fragments thereof that are conjugated to polyethylene glycol (PEG) moieties to increase their half-life in vivo (also known as pegylation). Methods of pegylating polypeptides are well known in the art (See, e.g., U.S. Pat. No. 6,552,170 and European Pat. No. 0,401,384 as examples of methods of generating pegylated polypeptides). In some embodiments, the isolated osteoinductive agent(s) are provided as fusion proteins. In one embodiment, the osteoinductive agent(s) are available as fusion proteins with the Fc portion of human IgG. In another embodiment, the osteoinductive agent(s) are available as hetero- or homodimers or multimers. Examples of some fusion proteins include, but are not limited to, ligand fusions between mature osteoinductive polypeptides and the Fc portion of human Immunoglobulin G (IgG). Methods of making fusion proteins and constructs encoding the same are well known in the art.

Isolated osteoinductive agents that are included within the graft material are typically sterile. In a non-limiting method, sterility is readily accomplished for example by filtration through sterile filtration membranes (e.g., 0.2 micron membranes or filters). In one embodiment, the graft material includes osteoinductive agents comprising one or more members of the family of Bone Morphogenic Proteins ("BMPs"). BMPs are a class of proteins thought to have osteoinductive or growth-promoting activities on endogenous bone tissue, or function as pro-collagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18 as well as polynucleotides or polypeptides thereof, as well as mature polypeptides or polynucleotides encoding the same.

BMPs utilized as osteoinductive agents comprise one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

In another embodiment, isolated osteoinductive agents that are loaded in the graft material include osteoclastogenesis inhibitors to inhibit bone resorption of the bone tissue surrounding the site of implantation by osteoclasts. Osteoclast and osteoclastogenesis inhibitors include, but are not limited to, osteoprotegerin polynucleotides or polypeptides, as well as mature osteoprotegerin proteins, polypeptides or polynucleotides encoding the same. Osteoprotegerin is a member of the TNF-receptor superfamily and is an osteoblast-secreted decoy receptor that functions as a negative regulator of bone resorption. This protein specifically binds to its ligand, osteoprotegerin ligand (TNFSF11/OPGL), both of which are key extracellular regulators of osteoclast development.

Osteoclastogenesis inhibitors that can be loaded in the graft material further include, but are not limited to, chemical compounds such as bisphosphonate, 5-lipoxygenase inhibitors such as those described in U.S. Pat. Nos. 5,534,524 and 6,455,541 (the contents of which are herein incorporated by reference in their entireties), heterocyclic compounds such as those described in U.S. Pat. No. 5,658,935 (herein incorporated by reference in its entirety), 2,4-dioxoimidazolidine and imidazolidine derivative compounds such as those described in U.S. Pat. Nos. 5,397,796 and 5,554,594 (the contents of which are herein incorporated by reference in their entireties), sulfonamide derivatives such as those described in U.S. Pat. No. 6,313,119 (herein incorporated by reference in its entirety), or acylguanidine compounds such as those described in U.S. Pat. No. 6,492,356 (herein incorporated by reference in its entirety).

In another embodiment, isolated osteoinductive agents that can be loaded in the graft material include one or more members of the family of Connective Tissue Growth Factors ("CTGFs"). CTGFs are a class of proteins thought to have growth-promoting activities on connective tissues. Known members of the CTGF family include, but are not limited to, CTGF-1, CTGF-2, CTGF-4 polynucleotides or polypeptides thereof, as well as mature proteins, polypeptides or polynucleotides encoding the same.

In another embodiment, isolated osteoinductive agents that can be loaded in the graft material include one or more members of the family of Vascular Endothelial Growth Factors ("VEGFs"). VEGFs are a class of proteins thought to have growth-promoting activities on vascular tissues. Known members of the VEGF family include, but are not limited to, VEGF-A, VEGF-B, VEGF-C, VEGF-D, VEGF-E or polynucleotides or polypeptides thereof, as well as mature VEGF-A, proteins, polypeptides or polynucleotides encoding the same.

In another embodiment, isolated osteoinductive agents that can be loaded in the graft material include one or more members of the family of Transforming Growth Factor-beta ("TGFbetas"). TGF-betas are a class of proteins thought to have growth-promoting activities on a range of tissues, including connective tissues. Known members of the TGF-beta family include, but are not limited to, TGF-beta-1, TGF-beta-2, TGF-beta-3, polynucleotides or polypeptides thereof, as well as mature protein, polypeptides or polynucleotides encoding the same.

In another embodiment, isolated osteoinductive agents that can be loaded in the graft material include one or more Growth Differentiation Factors ("GDFs"). Known GDFs include, but are not limited to, GDF-1, GDF-2, GDF-3, GDF-7, GDF-10, GDF-11, and GDF-15. For example, GDFs useful as isolated osteoinductive agents include, but are not limited to, the following GDFs: GDF-1 polynucleotides or polypeptides corresponding to GenBank Accession Numbers M62302, AAA58501, and AAB94786, as well as mature GDF-1 polypeptides or polynucleotides encoding the same. GDF-2 polynucleotides or polypeptides corresponding to GenBank Accession Numbers BC069643, BC074921, Q9UK05, AAH69643, or AAH74921, as well as mature GDF-2 polypeptides or polynucleotides encoding the same. GDF-3 polynucleotides or polypeptides corresponding to GenBank Accession Numbers AF263538, BC030959, AAF91389, AAQ89234, or Q9NR23, as well as mature GDF-3 polypeptides or polynucleotides encoding the same. GDF-7 polynucleotides or polypeptides corresponding to GenBank Accession Numbers AB158468, AF522369, AAP97720, or Q7Z4P5, as well as mature GDF-7 polypeptides or polynucleotides encoding the same. GDF-10 polynucleotides or polypeptides corresponding to GenBank Accession Numbers BC028237 or AAH28237, as well as mature GDF-10 polypeptides or polynucleotides encoding the same.

GDF-11 polynucleotides or polypeptides corresponding to GenBank Accession Numbers AF100907, NP_005802 or 095390, as well as mature GDF-11 polypeptides or polynucleotides encoding the same. GDF-15 polynucleotides or polypeptides corresponding to GenBank Accession Numbers BC008962, BC000529, AAH00529, or NP_004855, as well as mature GDF-15 polypeptides or polynucleotides encoding the same.

In another embodiment, isolated osteoinductive agents that can be loaded in the graft material include Cartilage Derived Morphogenic Protein (CDMP) and Lim Mineralization Protein (LMP) polynucleotides or polypeptides. Known CDMPs and LMPs include, but are not limited to, CDMP-1, CDMP-2, LMP-1, LMP-2, or LMP-3.

CDMPs and LMPs useful as isolated osteoinductive agents that can be loaded in the graft material include, but are not limited to, the following CDMPs and LMPs: CDMP-1 polynucleotides and polypeptides corresponding to GenBank Accession Numbers NM_000557, U13660, NP_000548 or P43026, as well as mature CDMP-1 polypeptides or polynucleotides encoding the same. CDMP-2 polypeptides corresponding to GenBank Accession Numbers or P55106, as well as mature CDMP-2 polypeptides. LMP-1 polynucleotides or polypeptides corresponding to GenBank Accession Numbers AF345904 or AAK30567, as well as mature LMP-1 polypeptides or polynucleotides encoding the same. LMP-2 polynucleotides or polypeptides corresponding to GenBank Accession Numbers AF345905 or AAK30568, as well as mature LMP-2 polypeptides or polynucleotides encoding the same. LMP-3 polynucleotides or polypeptides corresponding to GenBank Accession Numbers AF345906 or AAK30569, as well as mature LMP-3 polypeptides or polynucleotides encoding the same.

In another embodiment, isolated osteoinductive agents that can be loaded in the graft material include one or more members of any one of the families of Bone Morphogenic Proteins (BMPs), Connective Tissue Growth Factors (CTGFs), Vascular Endothelial Growth Factors (VEGFs), Osteoprotegerin or any of the other osteoclastogenesis inhibitors, Growth Differentiation Factors (GDFs), Cartilage Derived Morphogenic Proteins (CDMPs), Lim Mineralization Proteins (LMPs), or Transforming Growth Factor-betas (TGF-betas), as well as mixtures or combinations thereof.

In another embodiment, the one or more isolated osteoinductive agents that can be loaded in the graft material are selected from the group consisting of BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18, or any combination thereof; CTGF-1, CTGF-2, CGTF-3, CTGF-4, or any combination thereof; VEGF-A, VEGF-B, VEGF-C, VEGF-D, VEGF-E, or any combination thereof; GDF-1, GDF-2, GDF-3, GDF-7, GDF-10, GDF-11, GDF-15, or any combination thereof; CDMP-1, CDMP-2, LMP-1, LMP-2, LMP-3, and/or any combination thereof; Osteoprotegerin; TGF-beta-1, TGF-beta-2, TGF-beta-3, or any combination thereof; or any combination of one or more members of these groups.

In some embodiments, BMP-2, BMP-7 and/or GDF-5 may be used at a concentration of 1-2 mg/cc of the graft material. The concentrations of growth factor can be varied based on the desired length or degree of osteogenic effects desired. Similarly, one of skill in the art will understand that the duration of sustained release of the growth factor can be modified by the manipulation of the compositions of the graft material, such as for example, microencapsulation of the growth factor within polymers. The sustained release graft material can therefore be designed to provide customized time release of growth factors that stimulate the natural healing process.

The graft material of the present application may comprise other therapeutic agents. Exemplary therapeutic agents include but are not limited to IL-1 inhibitors, such Kineret® (anakinra), which is a recombinant, non-glycosylated form of the human interleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), quinapril (an inhibitor of angiotensin II, which upregulates TNF-α), interferons such as IL-11 (which modulate TNF-α receptor expression), and aurin-tricarboxylic acid (which inhibits TNF-α), may also be useful as therapeutic agents for reducing inflammation. It is further contemplated that where desirable a pegylated form of the above may be used. Examples of still other therapeutic agents include NF kappa B inhibitors such as antioxidants, such as dithiocarbamate, and other compounds, such as, for example, sulfasalazine.

Examples of therapeutic agents suitable for use also include, but are not limited to, an anti-inflammatory agent, analgesic agent, or a combination thereof. Anti-inflammatory agents include, but are not limited to, apazone, celecoxib, diclofenac, diflunisal, enolic acids (piroxicam, meloxicam), etodolac, fenamates (mefenamic acid, meclofenamic acid), gold, ibuprofen, indomethacin, ketoprofen, ketorolac, nabumetone, naproxen, nimesulide, salicylates, sulfasalazine [2-hydroxy-5-[-4-[C2-pyridinylamino)sulfonyl]azo]benzoic acid, sulindac, tepoxalin, and tolmetin; as well as antioxidants, such as dithiocarbamate, steroids, such as cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable analgesic agents include, but are not limited to, acetaminophen, bupivicaine, fluocinolone, lidocaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine, amitriptyline, carbamazepine, gabapentin, pregabalin, or a combination thereof.

The introduction or injection of the graft material of the present application may be achieved through a pressurizing syringe or similar fluid mover. The composition injected may be a highly viscous material or a less viscous or a more fluid material, for example, relative to the highly viscous bone cement material conventionally introduced to bond an implant to bone. Injecting a more fluid material, such as a material that is flowable or readily flowable at normal or atmospheric pressure under the influence of gravity, is different from injecting highly viscous material, which is not readily flowable at such conditions. In one embodiment, the fluid or more fluid bone growth material has a viscosity at room temperatures and at the time of injecting in a range of about 2,000 centipoise to about 50,000 centipoise or about 100,000 centipoise or about 2,000 centipoise to about 10,000 centipoise or about 10,000 centipoise to about 20,000 centipoise or about 30,000 centipoise to about 50,000 centipoise or about 50,000 centipoise to about 70,000 centipoise or about 70,000 centipoise to about 100,000 centipoise.

In some embodiments, the composition after setting has a pore size in the range of about 1 to about 250 microns in diameter. In another embodiment, pore sizes may be in the range of about 5 to about 200 microns or about 10 to about 100 microns in diameter.

USES

The compositions of the present invention may, for example, be used as bone void fillers at any fracture site, including but not limited to metaphyseal sites, such as those at the end of the tibia and femur, as well as at any other sites where there is bone void. They may used in many different organisms, including but not limited to in mammals such as humans.

Thus, the osteogenic osteoimplant (i.e., the bone graft material) of this invention is intended to be applied at a bone repair site, e.g., one resulting from injury, defect brought about during the course of surgery, infection, malignancy or developmental malformation. The osteoimplant can be utilized in a wide variety of orthopedic, periodontal, neurosurgical, oral and maxillofacial surgical procedures such as the repair of simple and compound fractures and non-unions; external and internal fixations; joint reconstructions such as arthrodesis; general arthroplasty; cup arthroplasty of the hip; femoral and humeral head replacement; femoral head surface replacement and total joint replacement; repairs of the vertebral column including spinal fusion and internal fixation; tumor surgery, e.g., deficit filling; discectomy; laminectomy; excision of spinal cord tumors; anterior cervical and thoracic operations; repairs of spinal injuries; scoliosis, lordosis and kyphosis treatments; intermaxillary fixation of fractures; mentoplasty; temporomandibular joint replacement; alveolar ridge augmentation and reconstruction; inlay osteoimplants; implant placement and revision; sinus lifts; cosmetic procedures; etc. Specific bones that can be repaired or replaced with the osteoimplant herein include the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal and metatarsal bones. Possible clinical applications would include e.g., the treatment of traumatic fractures, pathologic fractures, stress fractures, congenital defects or fractures, or operative defects in any bone of the body that would be treated with plate fixation. Fracture categories treated with the osteoimplant can include but not be limited to intraarticular or periarticular fractures; metaphyseal fractures; transverse, oblique, comminuted, and fragmented fractures; repair to non-fractured sites; defects due to periodontal disease or surgery; and other bone defects.

The composite may be applied to bone-contacting surfaces of implant devices as a bone cement. The material may be applied directly to bone defects acting as a bone filler or bone graft. Alternatively the composition may be used in conjunction with various fixation devices such as screws and plates. The material can act as a delivery system when pharmaceutically active agents are added to the matrix. Advantageously, the present material can be used as a bioabsorbable, composition to attach soft tissues (e.g., ligaments) to bone without the need of screws or nonabsorbable fixation devices. A feature of a preferred embodiment is the use of sugar to enhance the adhesive, bio-adsorption and osteoproliferative qualities of the material.

In some embodiments, the present invention provides a composition that affects the in-situ repair and adherence of body parts to each other and to adjacent structures. A feature of the present invention is that the adhesive can "set" at physiologic temperatures and pH within a short time (e.g., about 10-45 minutes or about 15-25 minutes or about 5-15 minutes or about 1-5 minutes or about 15 second to about 1 minute), and can be set within extremely short time (i.e. −15 second or less) with the assistance of a laser. Another feature of the invention is that the bio-material expands in vivo.

In some embodiments, the present invention comprises a kit. The kit may contain a composition that comprises an injectable settable cement, DBM fibers, cancellous bone chips, and a syringe for applying the composition. The kit may further comprise instructions for using the syringe and composition. In some embodiments, the syringe is preloaded.

The kit may comprise a predetermined amount of the composition. For example, there may be a volume of from about 1 cc to about 30 ccs or from about 2 ccs to about 20 ccs or from abut 3 ccs to about 15 ccs or from about 4 ccs to about 10 ccs.

In some embodiments, the present invention comprises a device. The device may contain a composition that comprises an injectable settable cement, DBM fibers, and cancellous bone chips. The device may for example be a preloaded syringe for applying the composition.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A bone graft material comprising fully demineralized bone matrix fibers, surface demineralized bone chips, polyethylene glycol (PEG), magnesium, and polymethyl methacrylate in an injectable settable cement, wherein the fully demineralized bone matrix fibers and the surface demineralized bone chips comprise between about 20% to about 60% by volume of the bone graft material.

2. A bone graft material of claim 1, wherein the magnesium comprises magnesium oxide.

3. A bone graft material of claim 2, wherein the injectable settable cement comprises monopotassium phosphate.

4. A bone graft material of claim 3, wherein the injectable settable cement further comprises tricalcium phosphate.

5. A bone graft material of claim 4, wherein the surface demineralized bone chips comprise cancellous and/or cortical bone chips.

6. A bone graft material of claim 5, wherein the cancellous bone chips are from about 0.5 mm to about 5 mm in diameter.

7. A bone graft material of claim 6, wherein the injectable settable cement comprises from about 15% to about 45% water by weight.

8. A bone graft material of claim 7, wherein the injectable settable cement comprises from about 25% to about 35% water by weight.

9. A bone graft material of claim 1 further comprising BMP.

10. A bone graft material of claim 1 further comprising an antibiotic.

11. A bone graft material of claim 1, wherein the bone graft material has a setting time of about 5 minutes to about 20 minutes.

12. A bone graft material of claim 1, wherein the fully demineralized bone matrix fibers comprise a coating of a water-soluble cellulose or a gelatin.

13. A bone graft material of claim 1, further comprising a filler comprising from about 0.1 wt. % to about 5 wt. % of the bone graft material.

14. A bone graft material of claim 13, wherein the filler comprises graphite or prolytic carbon.

15. A method for regenerating bone comprising injecting the bone graft material of claim 1 into a bone void.

16. A method according to claim 15, wherein the bone graft material is injected into a metaphyseal bone void.

17. A method according to claim 15, wherein the bone graft material is resorbed in a period of about 4 to about 8 months.

18. A method according to claim 17, wherein the bone graft material further comprises BMP.

19. A method according to claim 15, wherein the bone graft material further comprises an antibiotic.

20. A method according to claim 15, wherein the surface demineralized bone chips comprise cancellous and/or cortical bone chips.

* * * * *